United States Patent
Hettrick et al.

(10) Patent No.: US 7,729,764 B2
(45) Date of Patent: Jun. 1, 2010

(54) SYSTEM AND METHOD FOR IMPROVING PACING PARAMETERS USING ACUTE HEMODYNAMIC FEEDBACK DURING DEVICE IMPLANT

(75) Inventors: Douglas A. Hettrick, Blaine, MN (US); Paul D. Ziegler, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 595 days.

(21) Appl. No.: 11/095,790

(22) Filed: Mar. 31, 2005

(65) Prior Publication Data

US 2006/0224196 A1 Oct. 5, 2006

(51) Int. Cl.
*A61N 1/00* (2006.01)
(52) U.S. Cl. .............................. 607/27; 607/9
(58) Field of Classification Search ............... 607/9–28; 600/513, 515
See application file for complete search history.

(56) References Cited

U.S. PATENT DOCUMENTS

| | | | |
|---|---|---|---|
| 5,544,656 A | 8/1996 | Pitsillides et al. | |
| 6,277,077 B1 | 8/2001 | Brisken et al. | |
| 6,298,261 B1 | 10/2001 | Rex | |
| 6,795,732 B2 | 9/2004 | Stadler et al. | |
| 6,978,184 B1 * | 12/2005 | Marcus et al. | 607/120 |
| 7,194,306 B1 * | 3/2007 | Turcott | 607/17 |
| 7,228,175 B2 * | 6/2007 | Jain et al. | 607/17 |
| 2005/0027323 A1 | 2/2005 | Mulligan et al. | |

* cited by examiner

*Primary Examiner*—Scott M Getzow
(74) *Attorney, Agent, or Firm*—Stephen W. Bauer (57) ABSTRACT

The efficacy of cardiac resynchronization therapy applied to a patient's heart by an implantable device are improved by obtaining acute hemodynamic feedback during implantation of a pacing device. A first and a second transducer are temporarily placed proximate to a portion of the patient's heart during device implant, and a distance between the transducers is monitored as the therapy is applied. A parameter (e.g. lead location, biventricular pacing, pacing rate, or the like) of the cardiac therapy is adjusted in response to the distance between the transducers until a desired result is obtained, after which the first and second transducers can be removed from the patient.

12 Claims, 7 Drawing Sheets

SYSTEM AND METHOD FOR IMPROVING PACING PARAMETERS USING ACUTE HEMODYNAMIC FEEDBACK DURING DEVICE IMPLANT

TECHNICAL FIELD

The invention relates to cardiac therapy and, more particularly, to systems and techniques for optimizing pacing parameters using acute hemodynamic feedback during implantation of a pacing device.

BACKGROUND

Pacemakers and other implantable medical devices (IMDs) are becoming increasingly common. A conventional IMD is a battery-powered device that applies electrical impulses to a patient's heart to rectify arrhythmias. Typically, one or more electrodes are attached to the heart and coupled to the IMD via conductive leads. The electrodes and leads allow detection of electrical activity and also enables the delivery of electrical stimulus to the heart as appropriate.

As medical and computing technologies have progressed, IMDs have become increasingly capable of applying highly sophisticated and elaborate therapies, including pacing of multiple chambers of the heart. Such therapies can often be uniquely tailored to the particular needs of the patient, provided that adequate information about the patient is available while the device is being implanted and/or configured. The current state of the art is such that the techniques used for acutely identifying potential responders to cardiac therapy, at the time that the device is implanted in the patient, need substantial improvement.

In particular, the impact of atrial or ventricular lead placement can be difficult to evaluate while the device is being implanted. Early passive fixation leads typically required that leads be placed in specific regions of the ventricles in order to assure lead stability and long term performance. The advent of active fixation leads and left ventricular leads for cardiac resynchronization therapy now allows lead placement regions of the atria and ventricle that previously were not practical. Recent medical literature has described potential advantages of alternate site pacing lead placements in both the atrium and ventricles, including suppression of atrial and ventricular tachyarrhythmias, and improved symptoms of congestive heart failure. Despite this increased lead placement utility, however, few techniques are presently available to discriminate the relative advantage of various pacing lead sites.

It is therefore desirable to create a system and/or technique that is capable of identifying therapy responders during device implantation so that such information can be used to improve the effectiveness of applied therapy. Moreover, it is desirable to create a technique for optimizing lead placement or other parameters using hemodynamic information obtained at the time of implant. Furthermore, other desirable features and characteristics will become apparent from the subsequent detailed description and the appended claims, taken in conjunction with the accompanying drawings and this background section.

BRIEF DESCRIPTION

According to various exemplary embodiments, the effects of cardiac resynchronization therapy applied to a patient's heart by an implantable device are improved by obtaining acute hemodynamic feedback during implantation of a pacing device.

In various embodiments, first and second transducers are temporarily placed proximate to a portion of the patient's heart during device implant, and a distance between the transducers is monitored as the therapy is applied. A parameter (e.g. lead location, biventricular pacing, pacing rate, or the like) of the cardiac therapy is adjusted in response to the distance between the transducers until a desired hemodynamic result is observed, after which the first and second transducers can be removed from the patient.

In further exemplary embodiments, hemodynamic information is provided as feedback to a healthcare provider during implant of an IMD or cardiac resynchronization device. An ultrasonic signal is produced at a first temporary ultrasonic transducer, and an indication of the ultrasonic signal is received from a second temporary ultrasonic transducer. The indication is then processed to compute a hemodynamic parameter such as any index of ventricular synchrony, systolic function, diastolic function and/or the like. The hemodynamic parameter is then presented on a display to thereby allow the technician to adjust a parameter of the cardiac resynchronization device. By monitoring the hemodynamic status of the patient during implant of a resynchronization therapy device, the technician is able to ascertain lead locations and/or other pacing parameters that provide improved therapeutic response.

In still other embodiments, digital storage devices and/or systems incorporate similar concepts. These and other exemplary embodiments are described in additional detail below.

BRIEF DESCRIPTION OF DRAWINGS

Various exemplary embodiments will hereinafter be described in conjunction with the following drawing figures, wherein like numerals denote like elements, and.

DETAILED DESCRIPTION

The following detailed description is exemplary in nature and is not intended to limit the invention or the application and uses of the invention. Furthermore, there is no intention to be bound by any theory presented in the preceding background of the invention or the following detailed description of the drawings.

Hemodynamics is the study of the physical force generated by the heart to pump blood through the cardiovascular system, including such factors as blood pressure, blood flow and the like. A patient's hemodynamic status is known to be related to the overall health of the cardiovascular system, and a degraded hemodynamic status may be indicative of heart disease, hypertension, and/or other cardiac disorders. Conversely, hemodynamic information can be used to identify responders to pacing and other device-based therapies, and can be used to optimize (or at least improve) the effectiveness of such therapies.

Hemodynamic information may be obtained from ultrasonic signals transmitted between two or more piezoelectric sonomicrometer crystals or other ultrasonic transducers temporarily placed proximate to the patient's heart during the device implant procedure. The transducers may be positioned in an appropriate location with a guide catheter, an acute pacing lead or lead sheath, a guide wire or the like. In an exemplary embodiment, two transducers are temporarily placed near the patient's right ventricular apex and distal coronary sinus to monitor activity of the left ventricle, although alternate embodiments could use any number of transducers located at any points at or near the patient's heart as appropriate.

By tracking the time for the ultrasonic signal to propagate between the transducers, the dimensions of the heart (or a portion of the heart, e.g. an atrium or ventricle) can be ascertained and tracked as time progresses. This dimensional information can in turn be processed to deduce commonly described hemodynamic parameters such as stroke dimension or diameter (the total shortening of a measured cardiac segmental dimension during a cardiac cycle), percentage segment shortening (stroke diameter divided by maximal diameter), the ratio of early to late mitral valve blood flow velocity (E/A) wave amplitudes, indices of isovolumic contraction or expansion, and/or the like. Such hemodynamic information can be used to gauge the effectiveness of applied therapy, to identify responders to particular therapies and/or to adjust a parameter of an applied therapy. Pacing rates or timing parameters can be adjusted, for example, to produce improved hemodynamic response. Hemodynamic information at device implant could be further used to identify responders to IMD therapy, cardiac resynchronization therapy or other therapies. Moreover, because the response to cardiac resynchronization therapy (CRT) can depend upon the specific location of left ventricular, right ventricular and/or atrial leads, the hemodynamic data obtained from the transducers can be used by a technician during implant to place the leads at the locations on the patient's heart that provides the best response.

Figure 1:
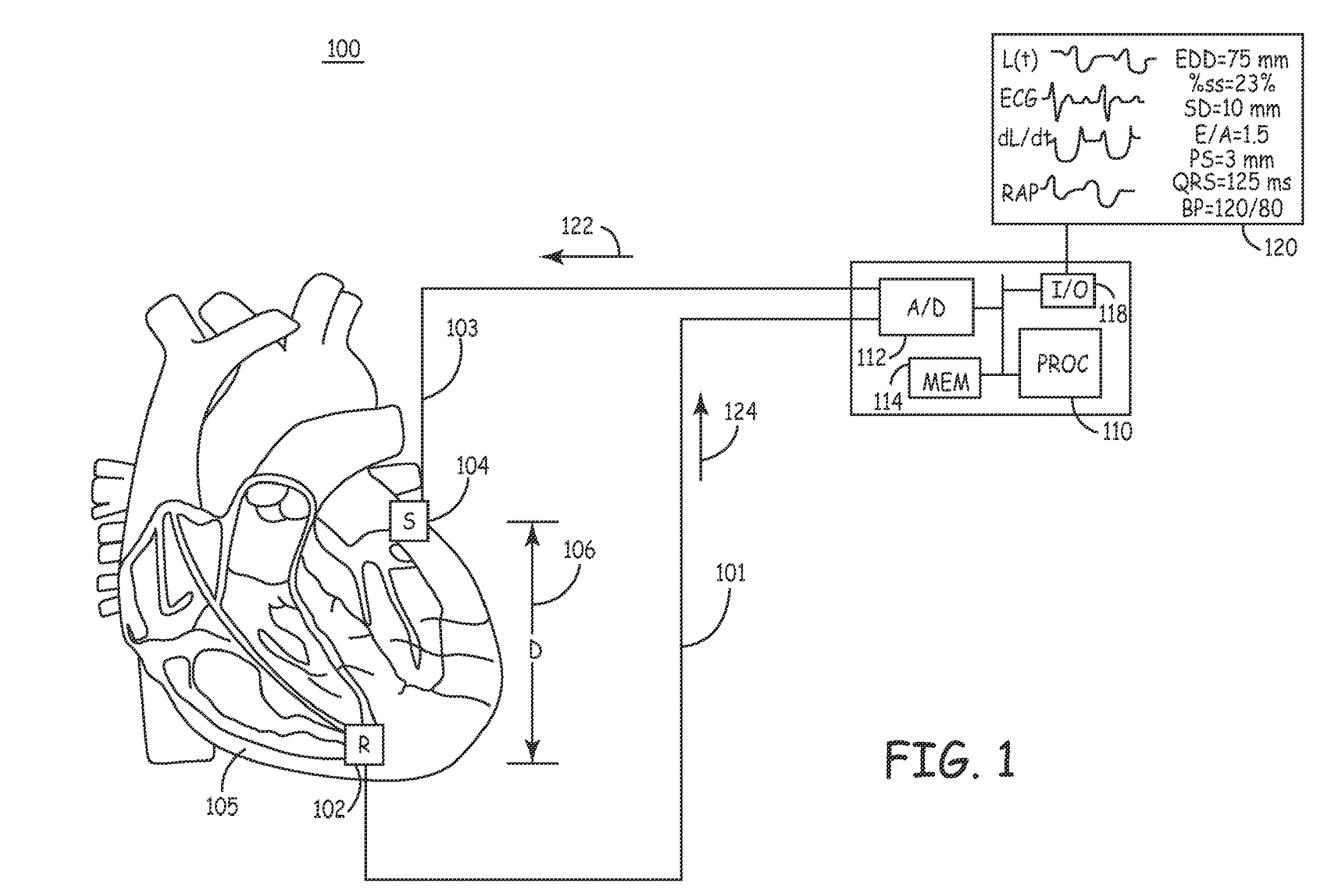
FIG. 1 is a diagram illustrating an exemplary system for obtaining hemodynamic information about a patient during implant of a medical device.

Turning now to the drawing figures and with initial reference to FIG. 1, an exemplary system 100 for providing acute hemodynamic feedback to a technician during implant of a cardiac resynchronization device suitably includes a controller 110 that communicates with two or more transducers 102, 104 and a display 120 as appropriate. Controller 110 transmits and receives electrical impulses 122, 124 via leads 101 and 103 that are indicative of ultrasonic signals transmitted between transducers 102 and 104. By monitoring ultrasonic signals transmitted through the patient's heart 105, controller 110 suitably processes and presents hemodynamic information to the technician on display 120 as appropriate.

Transducers 102, 104 are any sensors or other devices capable of converting electrical energy to mechanical energy, or vice versa. In various embodiments, transducers 102, 104 are implemented with conventional piezoelectric crystals of appropriate size for implantation within or near the patient's heart tissue. Such crystals could include, for example, the piezoelectric sonomicrometry crystals available from Sonometrics Corp. of London, Ontario, Canada, although other ultrasonic sensors could be used in other embodiments.

Transducers 102, 104 are placed as appropriate to obtain desired dimensional information about heart 105. Such placement may vary from embodiment to embodiment according to the particular task carried out by system 100. Through application of piezoelectric or other effects, distances 106 between transducers 102, 104 can be measured in real time. That is, measurements of distance 106 can be determined based upon the transit time of sound signals passed between two or more transducers 102, 104 and the speed of sound ($V_s$) in the particular medium, which is typically a known quantity (e.g. on the order of 1500 meters/second or so for water, blood or tissue, although particular values may vary from embodiment to embodiment). The relationship of this distance (D) 106 to the transit time ($\Delta t$) for the ultrasonic signals is conventionally expressed by the equation $D=V_s*\Delta t$.

In an exemplary implementation for obtaining hemodynamic information, transducers 102, 104 can be located near the patient's right ventricular apex and distal coronary sinus, respectively, to allow for convenient measurement of the patient's left ventricle. By monitoring the dimensions of the patient's left ventricle during systole, diastole, preload and/or synchrony, various observations and/or computations regarding the patient's hemodynamic status may be processed at controller 110, as described more fully below. Alternate embodiments may locate transducers 102, 104 at any other location at or near heart 105 to obtain other distance measurements (e.g. atrial dimension) as desired. The signal utilized to obtain such information may be the raw dimension signal itself, and/or other derived signals such as the derivative or integral of the dimension signal.

Controller 110 is any module, device or system capable of obtaining an indication 124 of distance 106 from one or more transducers 102, 104, of processing the indication signal to compute one or more hemodynamic parameters, and of causing the computed parameter to be presented to the technician on display 120. In the exemplary embodiment shown in FIG. 1, controller 110 includes a processor 116, a digital memory 114, an interface 112 to transducers 102, 104 and a video interface 118 to display 120, although alternate embodiments may contain additional and/or alternate components.

Processor 116 is any device or module capable of processing signals received from transducers 102, 104 to provide suitable outputs to display 120. In various embodiments, processor 116 is implemented with a conventional microprocessor, controller, digital signal processor, programmed logic array, application specific circuit and/or other integrated or discrete circuitry. Alternatively, the functions of processor 116 may be implemented with software executing on a general-purpose or other computer system. Processor 110 suitably executes instructions stored within memory 114. Such instructions may be executed in any manner, using any data structures, operating system constructs, architecture elements, programming languages and/or other techniques. Memory 114 is any storage medium capable of maintaining data and instructions provided to processor 116, such as any static or dynamic random access memory (RAM) or any other electronic, magnetic, optical or other storage medium.

Interface 112 is any circuit, module, card or other interface capable of exchanging electrical, electronic, optical or other signals 122, 124 with two or more transducers 102, 104. In various embodiments, interface 112 provides appropriate hardware ports for receiving leads 101, 103 as well as digital-to-analog and/or analog-to-digital conversion. Similarly, interface 118 is any video card, circuit, module, driver or other interface capable of converting instructions from processor 116 into electrical, electronic or other signals that can be processed and displayed on display 120.

Display 120 is any visual, audible or other interface capable of presenting information to a physician, aide or other human technician and/or an additional automated device capable of interpreting the information and adjusting therapy appropriately. Display 120 may be integrated within a common console with controller 110 in various embodiments, or may be logically and/or physically separated in any manner.

In various embodiments, the technician uses information presented on display 120 to assist in the implant of a cardiac resynchronization device or the like into a patient, as described more fully below. To assist in such endeavors, display 120 may present conventional cardiac information (e.g. electrocardiogram (ECG), right atrial pressure (RAP) and/or other information) as appropriate. Such information is typically obtained through conventional cardiac sensors. Additionally, display 120 suitably provides one or more hemodynamic data, such as end diastolic dimension (EDD), stroke diameter (SD), percent segment shortening (PSS or % SS), amplitudes of E or A waves, ratio of E/A wave amplitude, percent active filling, premature shortening (PS), isovoluminic lengthening (IL) and/or the like. A plot of ventricular dimension (L(t)) and/or the time derivative (dL/dt) of the ventricular dimension may also be provided as appropriate. The exemplary display 120 shown in FIG. 1 is one view that presents several of these hemodynamic and other parameters in conjunction with QRS duration and blood pressure (BP) data, although a wide array of alternate embodiments could display any sub-set, superset or other combination of additional or alternate parameters in any numeric, graphical or other manner.

In operation, then, system 100 suitably obtains, processes and displays hemodynamic information to provide feedback to a technician during implant of an IMD or cardiac resynchronization device. In an exemplary operating process, processor 116 directs the various operations of controller 110 using instructions and/or data stored in memory 114. Controller 110 appropriately directs 122 the transmission of an ultrasonic pulse (or other signal) from transducer 102 to transducer 104 (or vice versa). The receiving transducer 104 provides an indication 124 that the ultrasonic signal is received to controller 110, which appropriately determines the distance 106 between transceivers 102 and 104 from the response. While distance 106 may be determined in any manner, an exemplary embodiment simply records the difference in time between the transmission and receipt of the ultrasonic signal, and correlates this time to the distance using the relationship described above. The distance between the two transducers 102, 104 may then be further processed to determine hemodynamic data about the patient, which in turn is presented to the technician via display 120.

By monitoring the patient's hemodynamic status during implant of the device, the technician can make adjustments to various pacing parameters as appropriate to produce improved hemodynamic response. Such adjustments may include adjustments to the precise location of the pacing electrodes, for example, as described more fully below. Alternatively, the technician may adjust pacing rates or timing (e.g. a programmed atrio-ventricular delay and/or interventricular delay) to produce desired hemodynamic results. Further, the hemodynamic data can be used to identify potential responders to various therapies (e.g. bi-ventricular pacing) at the time of device implant. Additional detail about the correlation of cardiac dimensions to various hemodynamic parameters is set forth below.

Figure 2:
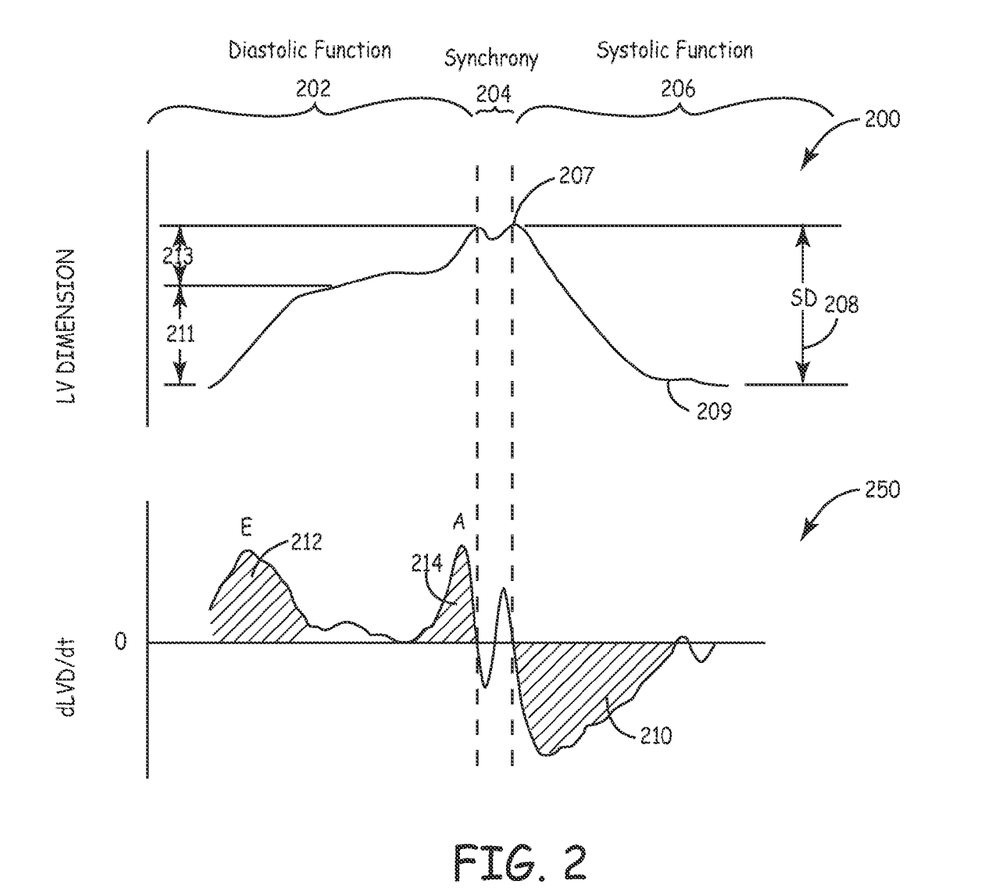
FIG. 2 is a diagram showing exemplary cardiac parameters that can be determined from ventricular dimension.

Various hemodynamic parameters can be derived from one or more observed atrial and/or ventricular dimensions. FIG. 2, for example, shows a plot 200 of an exemplary left ventricular dimension, along with a plot 250 showing the first time derivative of plot 200. Each plot 200, 250 is shown as observed over a complete beat cycle of heart 105 (FIG. 1). Generally speaking, plots 200 and 250 can be considered with respect to three time periods 202, 204 and 206 corresponding to diastolic function and preload, ventricular synchrony and systolic function, respectively. Plot 200 therefore shows ventricular dimension expanding during diastole and contracting during systole, as expected.

Using information shown in plots 200 and 250, various indices of the patient's hemodynamic state can be derived. Distances 211 and 213 in plot 200, for example, provide indices of passive and active ventricular filling, respectively, that can be used to evaluate diastolic function. Similarly, peaks "E" 212 and "A" 214 in plot 250 provide indices of peak mitral flow velocity during passive and active ventricular filling, respectively, further providing an indication of diastolic function. Other indices of diastolic function may include the ratio of A-wave amplitude 214 to E-wave amplitude 212 (i.e. E/A ratio), as well as the ratios of active or passive filling to the total amount of filling observed. Such ratios may be determined in any manner, including dividing distance 211 or 213 by the total of distances 211 and 213. Alternatively, the relative areas of A-wave 214 and E-wave 212 could be integrated over time and compared to the total area under plot 250 during diastolic period 202. Other parameters and/or calculation techniques could be used in alternate embodiments.

Similarly, various indices of systolic function could be determined from systolic portion 206 of plots 200 and/or 250. The stroke dimension or diameter (SD) 208, for example, could be computed as the difference between the end-diastolic dimension (EDD) 207 and the end-systolic dimension 209, as shown in FIG. 2. Stroke diameter is known to be analogous to the stroke volume of the patient's ventricle, and therefore may be useful in monitoring cardiac performance. Stroke diameter 208 may also be used to compute percent segment shortening (% SS), which is analogous to the patient's ejection fraction. Percent segment shortening may be computed by dividing the stroke diameter by the end-diastolic dimension, or according to any other technique. Stroke diameter and/or percent segment shortening may also be determined from integration of peak 210 of plot 250.

Figure 3:
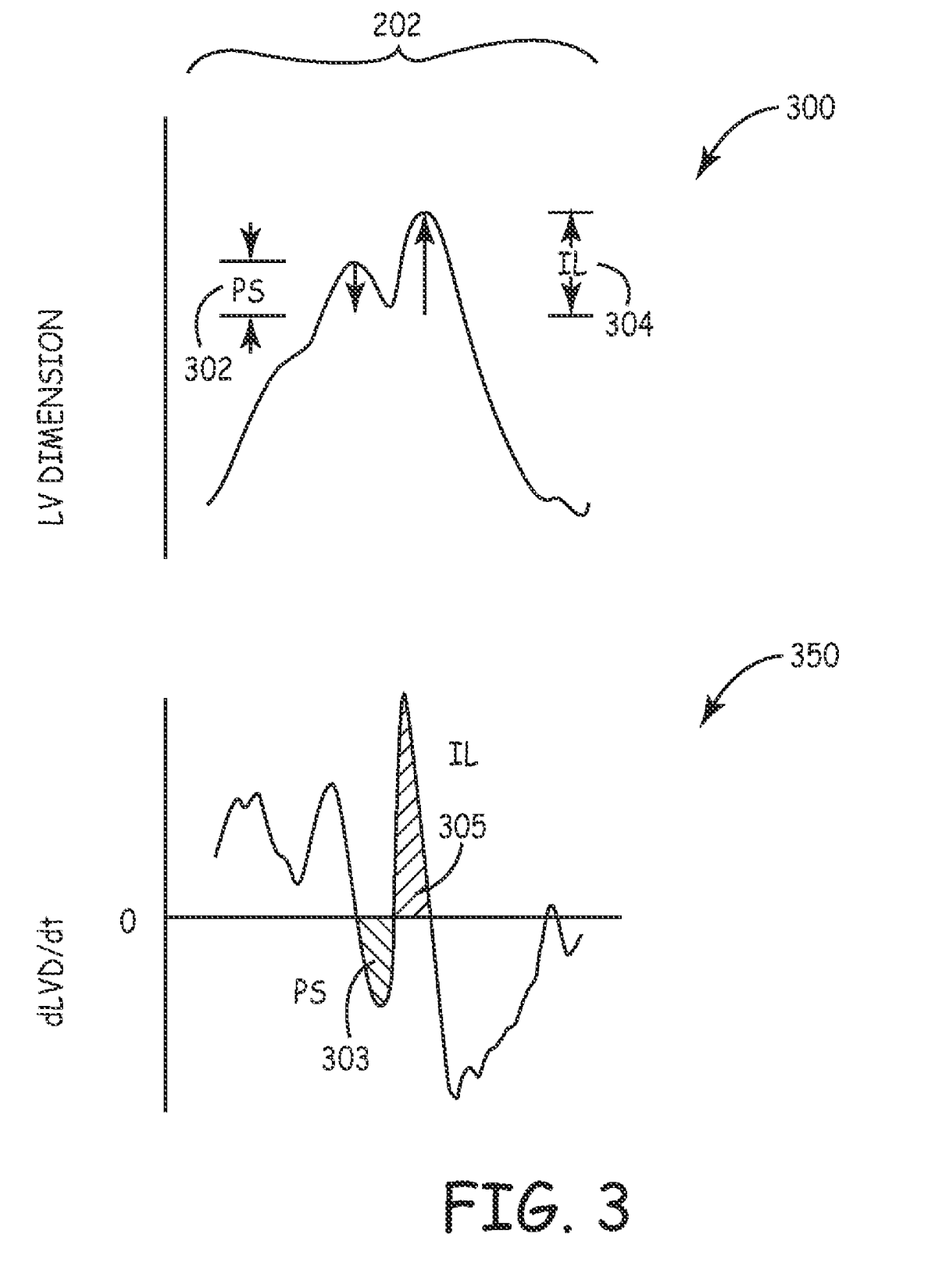
FIG. 3 is a diagram of exemplary cardiac parameters determined at synchrony.

Ventricular dimension during the period of isovolumic ventricular contraction or synchrony period 204, however, may be of particular interest in improving lead location, identifying potential therapy responders, and the like. FIG. 3 shows exemplary plots 300 and 350 of ventricular dimension and rate of change, respectively, during the expected period 204 of synchrony. The exemplary data of the particular plots 300 and 350 shown in FIG. 3, however, indicate a significant amount of undesirable asynchrony observed in the patient. That is, the ventricular dimension 300 shown in FIG. 3 exhibits both premature shortening (PS) 302 and isovolumic lengthening (IL) 304 of the ventricle during the time following diastole but prior to the opening of the aortic valve. These asymmetries can be identified through any conventional mathematical and/or signal processing techniques. Local maxima and/or minima can be recognized in ventricular dimension 300, for example, and/or non-zero rates of change can be identified in velocity data 350. Integrating velocity data 350 during period 204, for example, can show non-zero rates of change indicative of asymmetry.

A number of therapeutic options can be pursued using indices of symmetry determined from cardiac dimension. In various embodiments, indices of symmetry can be used to identify patients that are responders or non-responders to IMD cardiac resynchronization or other pacing therapies. That is, patients exhibiting asymmetry during temporary bi-ventricular pacing (or any other temporarily-applied therapy) can be immediately recognized as poor candidates for the therapy, which can be immediately discontinued. On the other hand, patients that exhibit improved symmetry during an applied therapy can be readily identified as a responder for that therapy. In addition to bi-ventricular pacing, therapies that can be evaluated in this manner include left ventricular pacing and/or alternate site pacing therapies. In the latter case, indices of synchrony are evaluated as pacing is applied at two or more locations on heart 105 (FIG. 1) to identify the pacing site that provides the best response and/or least asymmetry. Alternate site pacing therapies may variously include, without limitation, left and/or right ventricular pacing, right atrial pacing, dual site right atrial pacing, bi-atrial pacing, and/or the like.

Figure 4:
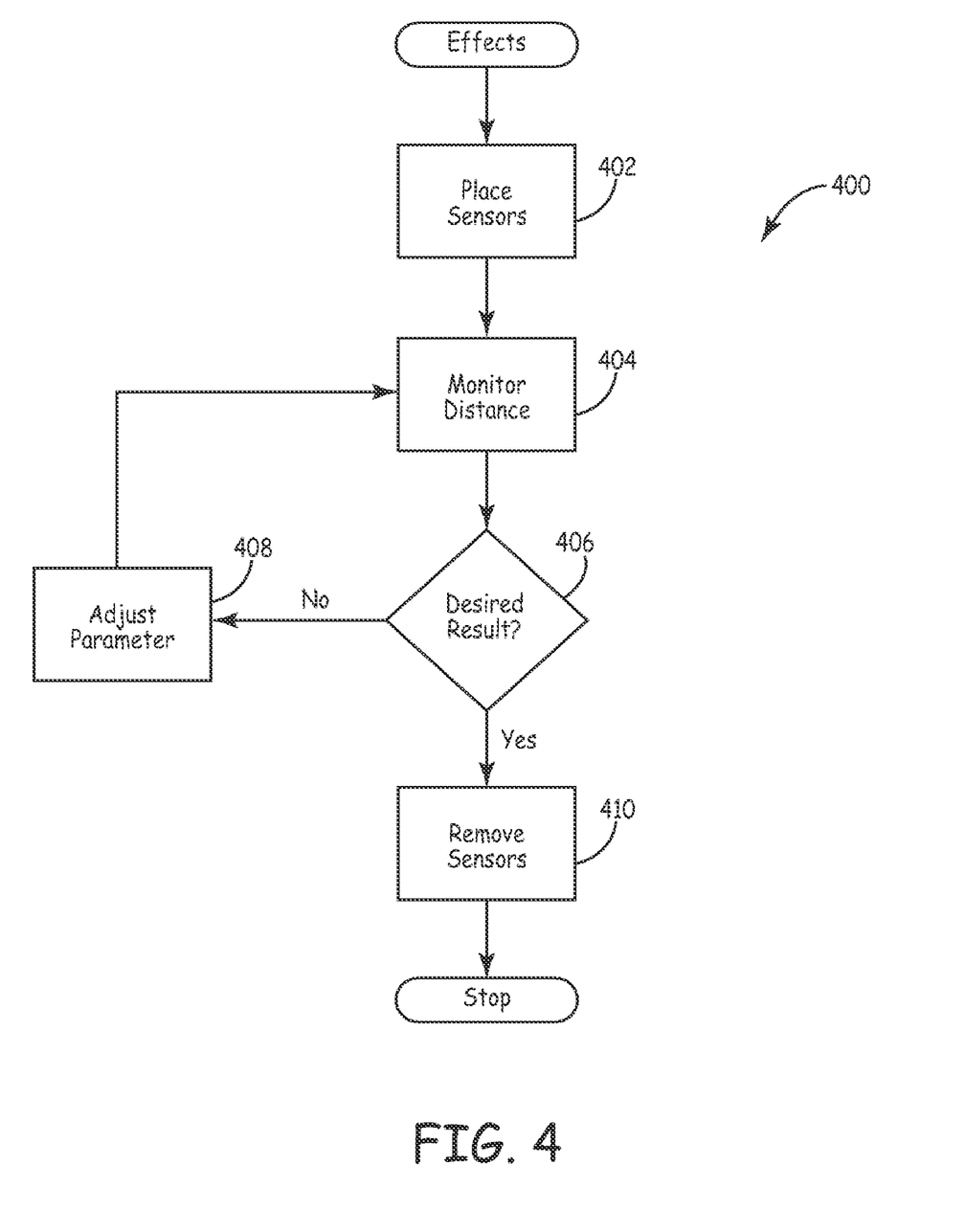
FIG. 4 is a flowchart of an exemplary process for improving resynchronization parameters based upon observed data.

With reference now to FIG. 4, an exemplary process 400 for improving the effects of cardiac resynchronization therapy suitably includes the broad steps of temporarily placing the transducer sensors at or near the patient's heart (step 402), monitoring the distance between the sensors as the heart responds to applied therapies (step 404), and adjusting a parameter of the applied therapy (step 408) until a desired result is obtained (step 406). After the result is obtained, the temporary sensors may be removed from the patient (step 410) as appropriate.

As described above, temporary sensor placement (step 402) occurs during implant of the pacing device so that one or more pacing parameters can be temporarily evaluated. Sensors (e.g. piezoelectric crystals or other transducers 102, 104 described above) may be placed in any appropriate location using any appropriate technique. In various embodiments, the sensors are mounted on a lead guide catheter sheath, on a lead guide-wire or on a temporary sensor lead, as described more fully in conjunction with FIGS. 5-7 below. Two or more sensors are therefore positioned near the patient's heart so that dimensional data of at least a portion of the heart (e.g. the right ventricle) can be evaluated.

After the sensors are in place, the technician appropriately monitors dimensional information obtained from the sensors (step 404) to improve the effectiveness of applied therapy. While the literal distance between sensors (e.g. the "L(t)" plot shown in display 120 of FIG. 1) may be present in some embodiments, in other embodiments, the distance information is further processed to obtain one or more hemodynamic parameters as described above. The technician need not literally monitor the distance between sensors, then, but rather may indirectly monitor the distance by evaluating a hemodynamic parameter (e.g. one or more indices of synchrony) obtained as a function of the distance between the sensors.

Using the acute hemodynamic information provided by the sensors, controller 110 and/or display 120 (FIG. 1), the technician is able to adjust pacing parameters (step 408) until a desired result is identified (step 406). Examples of pacing parameters that can be adjusted include pacing rates, pacing timing (e.g. atrio-ventricular (A-V) and/or right-to-left ventricular (V-V) delays), locations of electrodes, application of bi-ventricular or other pacing signals, and/or the like. The particular result desired in step 406 will vary depending upon the particular parameter being manipulated, but examples of desirable results may include reduction or elimination of wall motion during asynchrony, improved stroke diameter or E/A-wave ratio, and/or any other result.

Although not shown in FIG. 4, steps 404, 406 and 408 may be repeated for any number of additional pacing parameters. After the sensors are in place, for example, the technician may wish to identify optimal locations for pacing leads and evaluate the effectiveness of bi-ventricular or other pacing therapies. In such as case, pacing rate or timing may be further evaluated after lead locations are ascertained and appropriate therapies are determined but prior to removal of the sensors. Alternatively, multiple parameters may be simultaneously adjusted in step 408 to verify the hemodynamic effects as appropriate.

Transducer sensors 102, 104 may be placed at or near heart 105 in any appropriate manner. In various embodiments, any number of transducers 102, 104 are deployed using a temporary guide wire, temporary catheter (e.g. a guide catheter), guiding sheath used to place the pacing lead, and/or the like. Alternatively, an acute use transducer could be built into the lead for long-term placement inside the patient's body. Such a transducer could be activated during implant or lead revision, and/or could provide sensor data to the implanted device during continued operation. The various transducer placement techniques described herein may be combined, modified or supplemented as appropriate.

Figure 5:
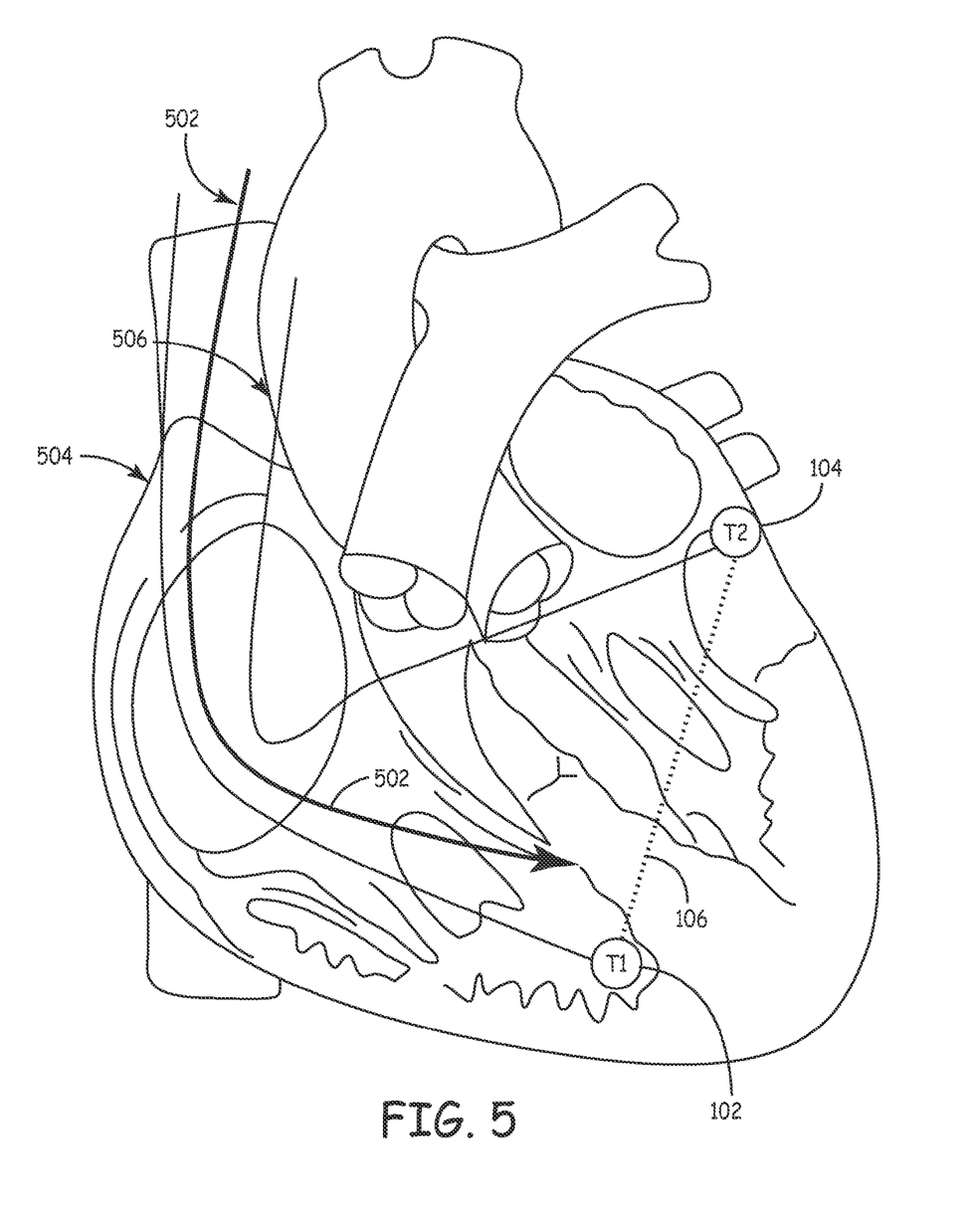
FIGS. 5-7 show exemplary techniques for obtaining ventricular dimensional data during lead placement.
Figure 6:
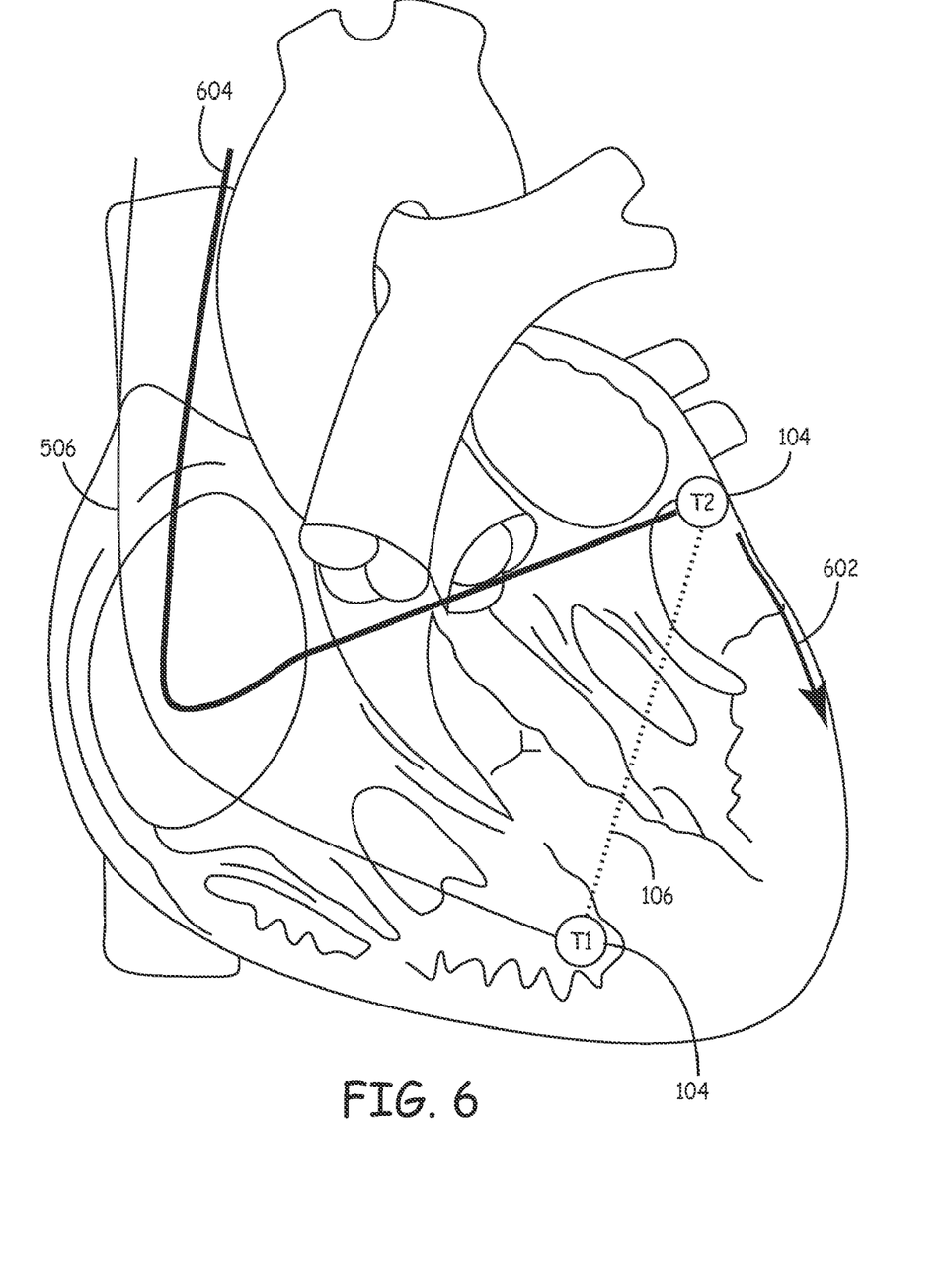
Figure 7:
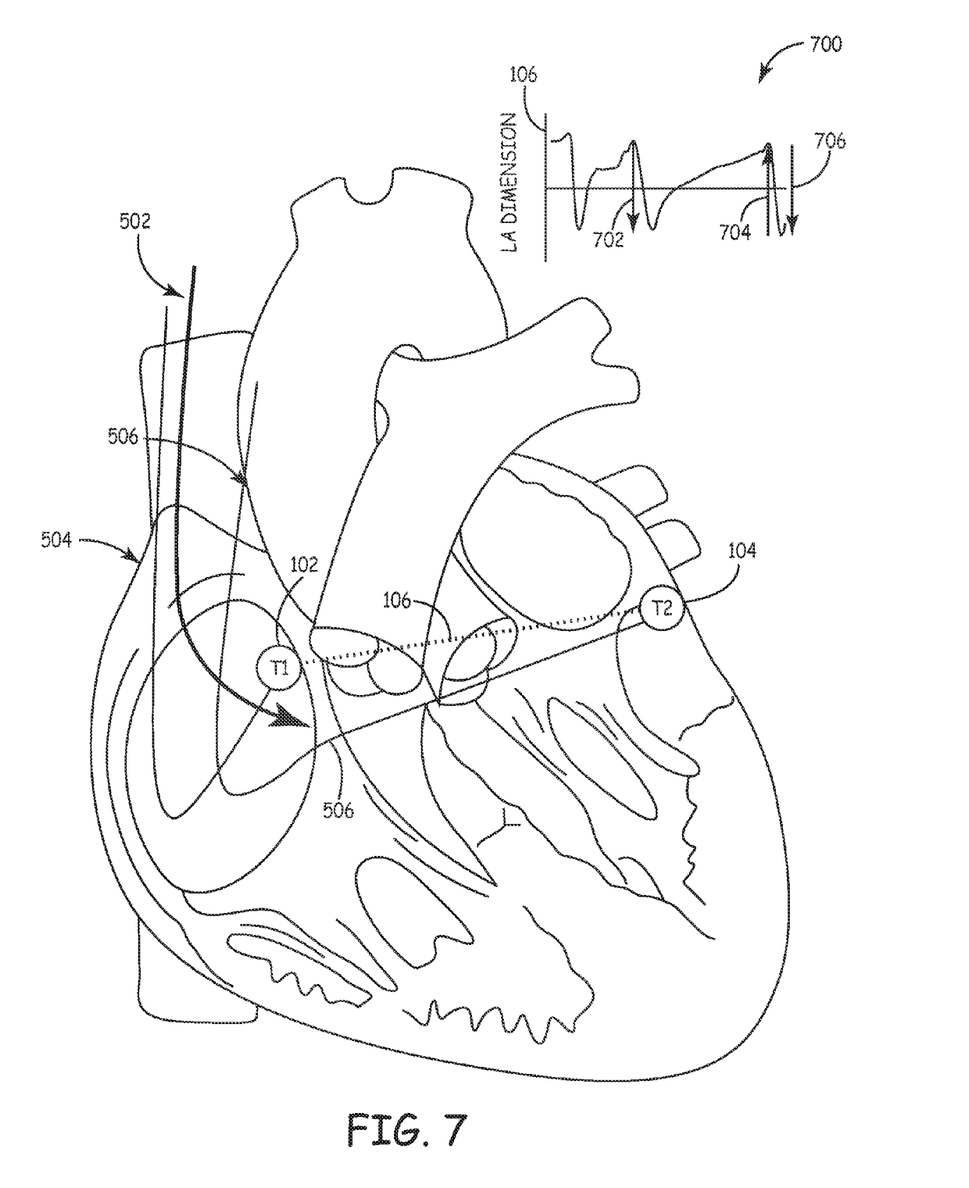

FIGS. 5-7 show three exemplary scenarios for placing ultrasonic transducer sensors 102, 104 proximate to a patient's heart 105 for calculation of a distance 106, although many alternate embodiments could be formulated. FIG. 5, for example, shows two transducers 102, 104 mounted on temporary guide catheters 504 and 506, respectively, for placement of a pacing lead 502 on the right ventricle of the patient's heart 105. Transducer 104 is shown located at the distal coronary sinus at the base of the posterior left ventricular free wall, and transducer 102 is shown located at the right ventricular apex, although either or both sensors could be located at other positions in other embodiments. As noted above, the position of lead 502 with respect to heart 105 can be adjusted as appropriate, with indications of distance 106 providing hemodynamic data that aids in the selection of an appropriate location.

FIG. 6 shows a similar scenario for placement of a left ventricular pacing lead 602 that is partially contained within a guiding catheter sheath 604. One of the transducers 102 is positioned on the sheath 604 as appropriate. Because sheath 604 is typically highly steerable within the intravascular space, transducer 102 may be located at or near the distal coronary sinus (or other desired location) while pacing lead 602 is positioned at various temporary locations near the left ventricle during the evaluation process 400 outlined above. Transducer 104 may be similarly placed on a guide or lead, or may be positioned using a guide catheter 506 as described above.

While the previous placement techniques focused primarily on ventricular lead placement and ventricular function, equivalent concepts could be applied to atrial function. FIG. 7, for example, shows an exemplary scenario for identifying optimal atrial lead locations or other features of atrial function. In the example shown in FIG. 7, transducers 102 and 104 are located on guide catheters 504 and 506 in the right atrial appendage and distal coronary sinus near the lateral base of the left atrium, respectively, although other locations (e.g. the high atrial septum) could be used in alternate embodiments.

Dimensions of the left and/or right atria may be processed in a manner similar to that described in FIGS. 2-4 above, or in any other appropriate manner. Plot 700 in FIG. 7, for example, shows an exemplary left atrial dimension 106 plotted over a complete beat cycle of heart 105 (FIG. 1) similar to the ventricular dimension shown above in FIG. 2. Plot 700, for example, shows various exemplary indices of passive emptying 702, refill 704 and/or active emptying 706. Such information may be quantified in terms of absolute distance 106, and/or according to time derivative, integral and/or other parameters as appropriate.

Atrial function is conventionally described in terms of conduit, reservoir, primary station and pump function, all of which may be evaluated using atrial dimensional information. Various indices of these functions could include the magnitude 702 of passive atrial emptying (PE), passive atrial strain (e.g. PE divided by the maximum passive dimension), magnitude 704 of refill dimension (RD), refill strain (RD divided by the maximum passive dimension), magnitude 706 of active emptying (AE), active strain (AE divided by the maximum passive dimension), and/or the like. Additional and/or alternate indices could be derived from the dimensional information 106 provided by transducers 102, 104 in any manner.

Further embodiments may incorporate three or more transducers to obtain information regarding both atrial and ventricular dimension. In such embodiments, atrial and ventricular dimensions could be analyzed to determine indices of atrio-ventricular mechanical coupling or the like. Such indices may variously include the ratio of atrial strain to ventricular strain, the ratio of total atrial emptying to total ventricular filling ((PE+AE) divided by SD) and/or the like. Such parameters could therefore provide insight into both atrial and left/right ventricular lead placement or other pacing parameters.

Accordingly, various methods and systems for identifying therapy responders and improving pacing parameters using data obtained from temporary ultrasonic transducers are provided. While exemplary embodiments have been presented in the foregoing detailed description of the invention, it should be appreciated that a vast number of equivalent variations exist. It should also be appreciated that these exemplary embodiments are only examples, and are not intended to limit the scope, applicability, or configuration of the invention in any way. Rather, the foregoing detailed description will provide a convenient road map for implementing an exemplary embodiment of the invention. Various changes may be made in the function and arrangement of elements described in an exemplary embodiment without departing from the scope of the invention as set forth in the appended claims and their legal equivalents.

The invention claimed is:

1. A method of improving the efficacy of cardiac resynchronization therapy, the method comprising:
   temporarily intravascularly placing a first and a second ultrasonic transducer proximate first and second portions of the patient's heart, wherein the placement location of said transducers is static relative to said first and second portions;
   monitoring distance between the first and second ultrasonic transducers;
   deriving hemodynamic parameters based on the distance;
   adjusting a location for lead placement of a lead for the cardiac resynchronization therapy in response to the hemodynamic parameters while maintaining the first and second ultrasonic transducers in the static placement location proximate the portion of the patient's heart;
   repeating the monitoring, deriving and adjusting steps until a desired result is obtained; and
   removing the first and second ultrasonic transducers after the desired result is obtained.

2. The method of claim 1 wherein the placing aspect comprises positioning at least one of the first and second ultrasonic transducers with a catheter.

3. The method of claim 1 wherein the placing aspect comprises positioning at least one of the first and second ultrasonic transducers with a pacing lead.

4. The method of claim 1 wherein the placing aspect comprises positioning at least one of the first and second ultrasonic transducers with a guide sheath encompassing a pacing lead.

5. The method of claim 1 wherein the placing aspect comprises positioning the first ultrasonic transducer proximate to a right ventricular apex of the patient's heart and the second ultrasonic transducer proximate to the distal coronary sinus of the patient's heart.

6. The method of claim 1 wherein the desired result includes reduction in wall motion during isovolumic contraction of a patient's heart.

7. A method of providing feedback to a healthcare provider during implant of an implantable medical device, the method comprising:
   intravascularly temporarily placing a first temporary ultrasonic sensor at a first location proximate and static relative to a first portion of the patient's heart and a second temporary ultrasonic sensor at a second location proximate and static relative to a second portion of the patient's heart;
   causing an ultrasonic signal to be produced at the first temporary ultrasonic sensor;
   receiving an indication of the ultrasonic signal from the second temporary ultrasonic transducer, wherein said first and second ultrasonic transducers are maintained in the first and second locations;
   processing the indication to compute a hemodynamic parameter;
   causing the hemodynamic parameter to be presented on a display;
   adjusting the placement location of a lead for an implantable medical device based on the displayed hemodynamic parameter while maintaining the first and second transducers in the first and second locations; and
   subsequently removing the first and second ultrasonic transducers.

8. The method of claim 7 wherein the hemodynamic parameter includes an index of ventricular synchrony.

9. The method of claim 7 wherein the hemodynamic parameter includes stroke diameter.

10. The method of claim 7 wherein the hemodynamic parameter includes percentage segment shortening.

11. The method of claim 7 wherein the hemodynamic parameter further comprises an index of peak mitral flow velocity during ventricular filling.

12. The method of claim 7 wherein a digital storage medium having computer-executable instructions stored thereon, wherein the instructions are configured to execute provision of feedback.

* * * * *